(12) United States Patent
Davis, III et al.

(10) Patent No.: US 7,416,757 B2
(45) Date of Patent: Aug. 26, 2008

(54) METHOD OF MAKING ACTIVE EMBOLIC COIL

(75) Inventors: Richard Champion Davis, III, Hollywood, FL (US); Yufu Li, Bridgewater, NJ (US); Zhigang Li, Hillsborough, NJ (US); Juan A. Lorenzo, Davie, FL (US); Murty N. Vyakarnam, South Orange, NJ (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 352 days.

(21) Appl. No.: 11/100,171

(22) Filed: Apr. 6, 2005

(65) Prior Publication Data

US 2005/0261727 A1   Nov. 24, 2005

Related U.S. Application Data

(60) Provisional application No. 60/560,652, filed on Apr. 8, 2004.

(51) Int. Cl.
*B05D 3/12* (2006.01)
*A61B 1/267* (2006.01)
*A61B 1/00* (2006.01)

(52) U.S. Cl. .............. 427/2.1; 427/2.24; 427/171; 600/200; 600/108

(58) Field of Classification Search ........... 427/2.24, 427/2.12, 175, 176, 2.25, 171, 2.1; 118/26, 118/28, 30, 33, 400, 404, 419, 420, 421, 118/423, 500; 606/108, 200; 600/585
See application file for complete search history.

(56) References Cited

U.S. PATENT DOCUMENTS

| | | | |
|---|---|---|---|
| 1,965,891 A * | 7/1934 | French | 118/400 |
| 2,050,830 A | 8/1936 | Delany | |
| 2,771,856 A | 11/1956 | Ardizzone et al. | |
| 3,073,713 A * | 1/1963 | Brodenr | 427/176 |
| 4,045,418 A | 8/1977 | Sinclair | |
| 4,057,537 A | 11/1977 | Sinclair | |
| 4,605,730 A | 8/1986 | Shalaby et al. | |
| 5,108,407 A | 4/1992 | Geremia et al. | |
| 5,122,136 A | 6/1992 | Guglielmi et al. | |
| 5,133,739 A | 7/1992 | Bezwada et al. | |
| 5,224,994 A * | 7/1993 | Daly | 118/53 |

(Continued)

FOREIGN PATENT DOCUMENTS

WO    WO 02/089865    11/2002

(Continued)

OTHER PUBLICATIONS

U.S. Appl. No. 10/738,477, Jones et al.

(Continued)

*Primary Examiner*—William P. Fletcher, III
*Assistant Examiner*—Cachet I Sellman
(74) *Attorney, Agent, or Firm*—George H. Gerstman; Sayfarth Shaw LLP

(57) ABSTRACT

A polymeric coating is applied to at least one embolic coil carried in a fixture, at least a portion of said embolic coil being generally vertical and straight. The coil is carried in the fixture during the processing, and may remain in the fixture if desired for further steps of processing.

18 Claims, 6 Drawing Sheets

U.S. PATENT DOCUMENTS

| | | | |
|---|---|---|---|
| 5,334,210 A | 8/1994 | Gianturco | |
| 5,382,259 A | 1/1995 | Phelps et al. | |
| 5,468,253 A | 11/1995 | Bezwada et al. | |
| 5,645,931 A | 7/1997 | Fan et al. | |
| 5,690,671 A | 11/1997 | McGurk et al. | |
| 5,713,920 A | 2/1998 | Bezwada et al. | |
| 5,725,534 A * | 3/1998 | Rasmussen | 606/108 |
| 5,820,676 A * | 10/1998 | Bauerle | 118/421 |
| 5,853,418 A | 12/1998 | Ken et al. | |
| 5,980,550 A | 11/1999 | Eder et al. | |
| 6,214,115 B1 | 4/2001 | Taylor et al. | |
| 6,287,318 B1 | 9/2001 | Villar et al. | |
| 6,306,424 B1 | 10/2001 | Vyakarnam et al. | |
| 6,333,029 B1 | 12/2001 | Vyakarnam et al. | |
| 6,355,699 B1 | 3/2002 | Vyakarnam et al. | |
| 6,365,149 B2 | 4/2002 | Vyakarnam et al. | |
| 6,462,086 B1 | 10/2002 | Kloog et al. | |
| 6,534,084 B1 | 3/2003 | Vyakarnam et al. | |
| 6,565,659 B1 | 5/2003 | Pacetti et al. | |
| 6,569,179 B2 | 5/2003 | Teoh et al. | |
| 6,607,598 B2 * | 8/2003 | Schwarz et al. | 118/500 |
| 6,623,508 B2 | 9/2003 | Shaw et al. | |
| 2002/0087184 A1 | 7/2002 | Eder et al | |
| 2002/0151915 A1 | 10/2002 | Hieshima et al. | |
| 2002/0177855 A1 | 11/2002 | Greene, Jr. et al. | |
| 2002/0193823 A1 | 12/2002 | Wallace et al. | |
| 2003/0093087 A1 * | 5/2003 | Jones et al. | 606/108 |
| 2003/0203991 A1 | 10/2003 | Schottman et al. | |
| 2005/0021074 A1 * | 1/2005 | Elliott | 606/200 |

FOREIGN PATENT DOCUMENTS

WO     WO 03/015640     2/2003

OTHER PUBLICATIONS

U.S. Appl. No. 10/738,473, Jones et al.

* cited by examiner

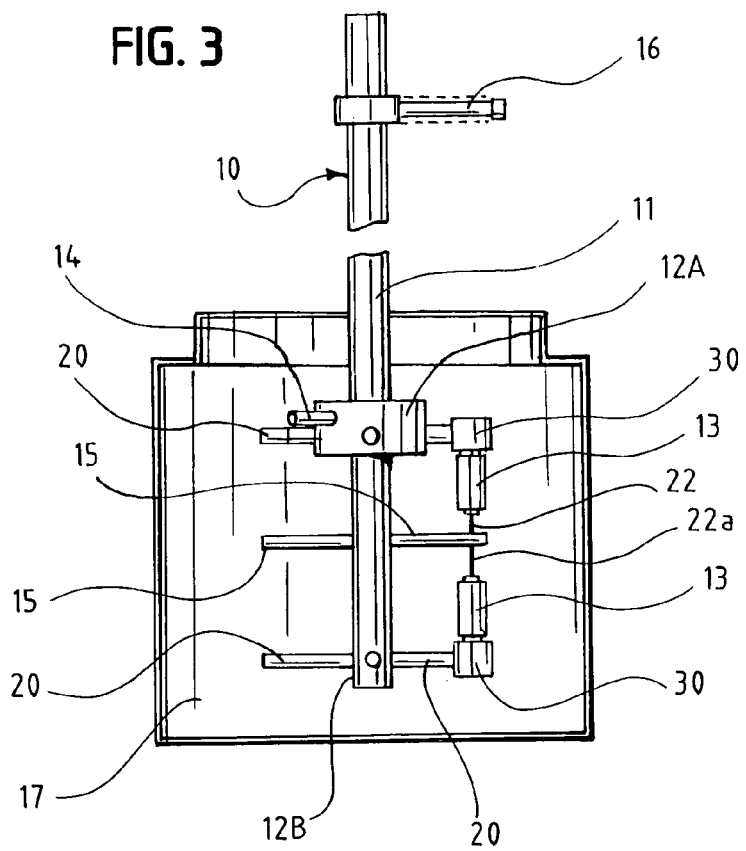
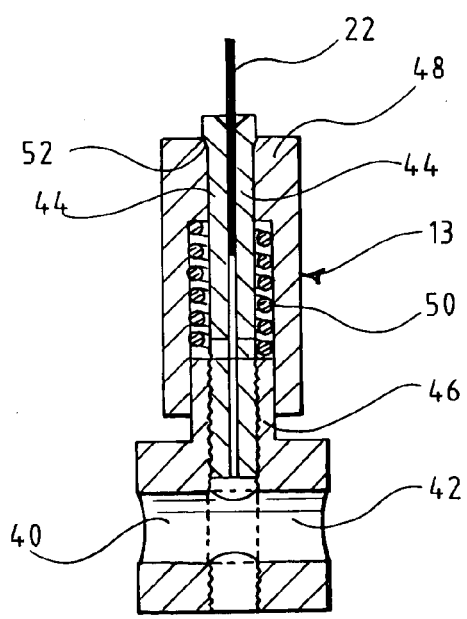

METHOD OF MAKING ACTIVE EMBOLIC COIL

This application claims priority from Provisional Application Ser. No. 60/560,652, filed Apr. 8, 2004.

BACKGROUND OF INVENTION

Field of the Invention

Embolic coils to treat aneurysms have tremendous advantages over neurosurgical clipping and are quickly becoming the standard of care. While coiling is the standard endovascular treatment option for many aneurysms, there is a large population of aneurysms that re-canalize over time. Once recanalization occurs, the coils may compact or the aneurysm may grow in size. In addition, these aneurysms are more susceptible to rupture. One potential concept to reduce the likelihood of recanalization is to cause tissue in-growth within the aneurysm to provide long-term treatment of the aneurysm. The disclosure describes a unique bioactive coating that encourages tissue ingrowth providing a long term solution to the problem of recanalization.

Further, the key to treating aneurysms lies in creating an optimum packing density within the aneurysm sack. Often coils do not fill and pack the aneurysm sack well and/or are difficult to deploy. This invention discloses an improved device that comprises a unique coating that overcomes both the issues of deployment and recanalization, and a method for such coating. This coating modulates the tissue response in such a way that rather than triggering a severe thrombolytic response it induces mild to moderate inflammatory response that promotes organization of fibrotic tissue leading to a more permanent treatment for aneurysms. The coating comprises a unique bioresorbable and biocompatible material that is also elastomeric in nature, for example as disclosed in Jones et al. U.S. patent application Ser. No. 10/811,753, filed Mar. 29, 2004.

The formation of fibrotic tissue decreases the chances for recanalization, thereby creating a safer and efficacious device. Unlike collagen based coatings, this coating is not prothrombolytic, thereby allowing the surgeon to manipulate its precise location for deployment. Further, the coating does not greatly alter the physical characteristics of the coil, which makes its deployment consistent.

The composition of the elastomeric polymer typically comprises caprolactone and glycolide components. The unique combination of these monomers results in an elastomeric copolymer which, when used to coat embolic coils using the methods disclosed herein results in flexible coils that retain their shape. The pro-inflammatory response can be easily monitored by changing the amount of the polymer coated on the device, changing the ratio of the composition, or by addition of low molecular weight glycolide or glycolic acid monomer.

Typically the embolic coils are metallic coils that are introduced in the neurovascular space using an image guided system. The coils are preformed during manufacturing to attain random or helical shapes that easily conform to a space. Once deployed at the proper location such as an embolism sac, they are detached from the delivery system, such as a microcatheter. The coils retain their preformed shapes to ensure integrity of the fill and to eliminate any migration of the coil from the sac into the vasculature. Coating the embolic coil poses significant challenges due to its inherent physical characteristics, pre-set configuration as well as the delicate attachment means to the microcatheter.

DESCRIPTION OF THE INVENTION

There are disclosed herein several methods of coating this device without compromising the coil shape and deployment characteristics. The preferred method of making such a device is by dip coating the embolic coil in the polymer solution. The method disclosed coats the coils using a fixture that unwinds the coils from its inserter package and/or straightens them, and dips them into a solution comprising a solvent or a mixture of solvents and a polymer. The coil gets coated in the solution, and is pulled out of the solution at a controlled speed, ensuring that the coil does not wrap on itself, straightening the coil without stretching as the coil is pulled out of the solution, which prevents the post-coating coil on coil adhesion. This pulling out also drains the excess solution. This process enables a uniform coating of the coil. Further embodiments of this coating process can include a drying step and an annealing step to provide a solvent-free and stable coating that has a long shelf life.

It is often beneficial to coat medical devices so that the surfaces of such devices have desired properties or effects. Medical devices generally are coated by processes such as dipping, and spraying. Although these processes have been previously used to produce satisfactory coatings, there are many issues associated with the processes for coating of those medical devices that are very soft, are helically or random shaped, and which cannot withstand forces resulted from the processes, even very tiny forces, resulting in uneasily (difficult) holding, coating defects due to the holding, nonuniform coating, and sticking. Another issue is that many processes require multiple coating steps for the application of a second coating material, or stages to allow for drying and annealing between coating steps, or after the final coating step. It is also needed that a coating process is cost-effective and productive.

Particularly, by this invention a method is provided for applying a polymeric coating to at least one embolic coil. This method comprises: passing one end of the embolic coil through an aperture in a spreading member to straighten the coil; attaching the one end of the embolic coil to an upper holder positioned above the spreading member, the upper coil portion that extends from the upper holder to the aperture being generally vertical and straight.

One then applies to the embolic coil, by dipping, spraying, or the like, a dispersion of a polymeric coating formulation in a solvent, while passing portions of the embolic coil which are below the spreading member upwardly through the spreading member, to cause substantially the entire embolic coil to be vertical and straight, with the embolic coil then rising above the surface of the coating formulation when dipping is used.

One removes the spreading member and the upper holder, while they are in fixed position relative to each other, typically held as parts of a fixture, while also removing the embolic coil from further contact with the coating formulation. Thereafter, one dries the embolic coil, typically before releasing it from its attachment to the upper holder and spreading member.

Typically, a portion of the embolic coil positioned below the spreading member is generally bunched into a wad of curved, bunched embolic coil portions, especially in those embodiments of embolic coil which spontaneously bunch together into such a wad of coil portions in their natural, unstretched configuration, so as to fit into an embolism sack.

In some embodiments, a lower end of the embolic coil is attached to a lower holder, which lower holder is held in fixed position relative to the spreading member. The upper holder can rise, and the spreading member is stationary, being immersed in the dispersion when the dispersion of a polymeric coating is applied to the embolic coil by immersing it into a container holding the dispersion. The relative rising of the upper holder causes portions of the embolic coil to pass upwardly through the spreader member, as described above, to straighten and hold vertical substantially the entire embolic coil, as it passes out of the dispersion, to facilitate the application of the polymer dispersion to the coil and the draining of excess coating formulation. It is preferred for that portion of the embolic coil which is emerging through the surface of the polymer dispersion to be vertical and straight, for uniform coating. In some embodiments, the container which holds the polymeric dispersion coating formula can be removed from further contact with the embolic coil by lowering of the container.

Preferably, a plurality of the upper holders and spreading members are present, holding a plurality of embolic coils in the manner described above. A plurality of lower holders may also be applied to secure the lower ends of the embolic coils.

After application of the polymeric coating to the embolic coil, by dipping as described above, spraying or any other desired technique, the embolic coils may be further processed prior to their removal from the upper holder and spreading member. The entire fixture system comprising one or a plurality each of upper holders and spreading members, and optionally lower holders, carrying one or a plurality of embolic coils, may be removed from the dipping or spray unit, and may be transported to another station, for further processing.

It is generally preferred for the embolic coil to be vertically held between the spreading member and the upper holder in a manner whereby individual coils of the embolic coil are spaced from each other, to facilitate access of the polymeric coating between the coils. This spacing of the individual coils may, for example, be a distance of about 0.0001 to 0.1 inch, preferably about 0.0003 to 0.005 inch.

In another aspect of this invention, a method is provided of applying a polymeric coating to a plurality of embolic coils, which comprises the steps of attaching said embolic coils to a fixture for supporting and mounting said coils with at least a portion of each of the coils positioned vertically and straight; and applying polymeric coating to the embolic coils by dipping the fixture and attached embolic coils into a dispersion of a polymeric coating formulation in a solvent, or otherwise applying said polymeric coating to said embolic coil such as by spraying; removing the fixture and the plurality of embolic coils from said formulation while at least a major portion of said coils are vertical and straight; and drying the embolic coils prior to removal from the fixture.

If desired, added processing steps of various kinds may also be applied to the embolic coils as they remain carried in the fixture.

Such a fixture permits the coating of multiple, embolic coils at the same time, and moving them for drying and subsequent processing, before they are removed from the fixture, resulting in an increase of manufacturing efficiency.

As before, it is preferred that the coils being treated are straight and vertical, with individual coils of each embolic coil being slightly spaced from each other to facilitate coating with polymeric coating between the coils.

DESCRIPTION OF THE DRAWINGS

In the drawings,

FIG. 3 is an elevational view of an embodiment similar to the device of FIGS. 1 and 2.

FIG. 4 is a longitudinal, sectional view of a holder which may be used in the embodiment of FIGS. 1-3 to hold and retain an end of the embolic coil.

FIG. 5 is a fragmentary, longitudinal, sectional view of the spreading members usable with the embodiments of FIGS. 1-3.

DESCRIPTION OF SPECIFIC EMBODIMENTS

The invention relates to a fixture and a method well suited to coating medical devices that are very soft, helically or random shaped, and very weak, and are easily stretched out even by a tiny force, and, sometimes, have a big ratio of length vs. diameter.

Figure 1:
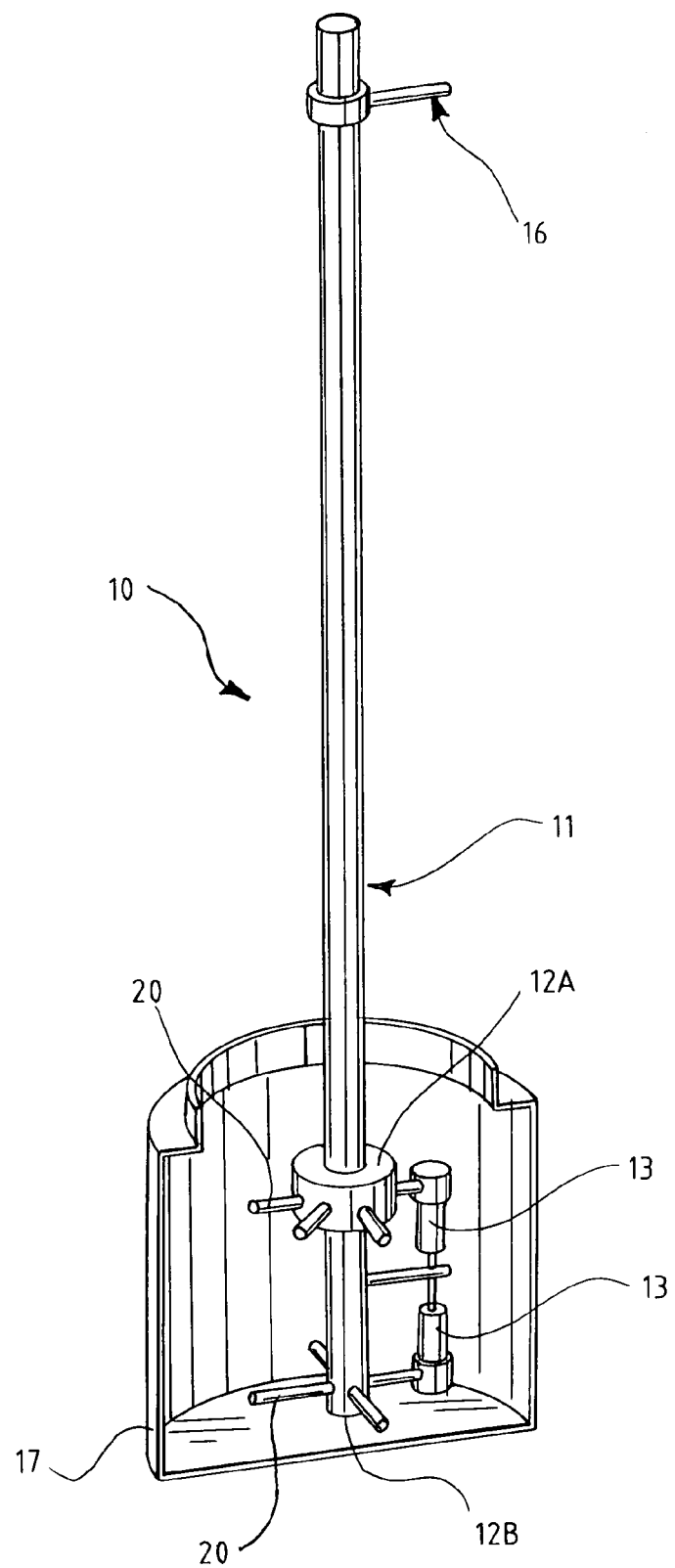
FIG. 1 is a perspective view, with portions broken away, of a fixture for supporting and mounting embolic coils for application of the polymeric coating, and other processing steps if desired.
Figure 2:
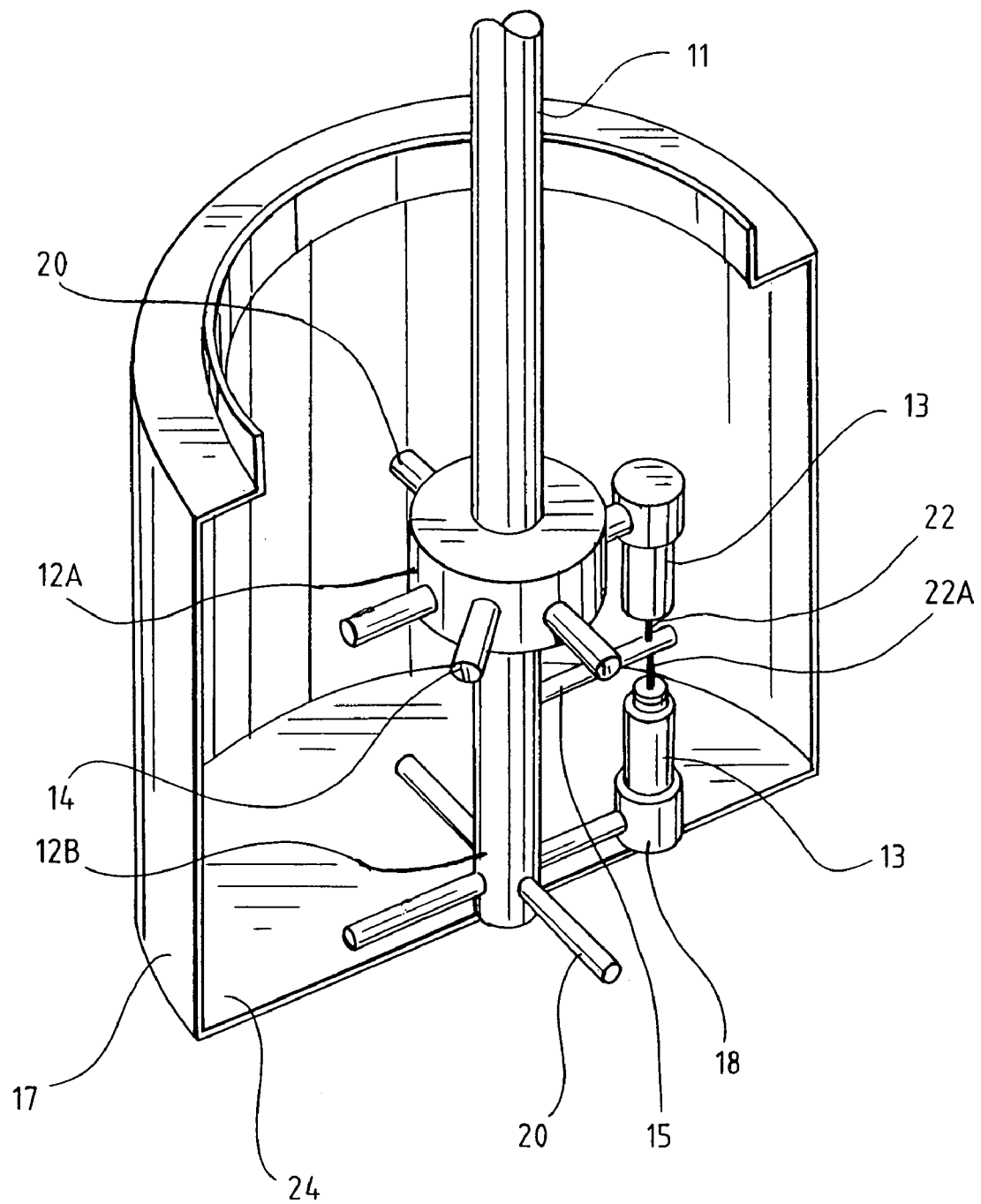
FIG. 2 is an enlarged, fragmentary version of the fixture of FIG. 1, with portions broken away, showing a single embolic coil, upper holder, spreading member, and lower holder, with added sites for other embolic coils and coil retaining equipment being shown.

Referring to FIGS. 1 and 2, the fixture 10 for supporting and mounting coils 22 is illustrated to include a supporting bar 11, holder bases 12A, 12B, holders 13, locating pin 14, spreading members 15 (just one shown here), and a range adjuster 16. The holder bases 12A, 12B have mounting rods 20, and four rods are shown on each holder base. The holder base 12B is unmovably fixed to the supporting bar 11. The holder base 12A is movable along the supporting bar 11, and is firstly positioned close to the holder base 12B carried on a locating pin 14 when coils 22 are being loaded to the fixture 10. The holders 13 are employed by pair, and are attached to the holder bases 12A, 12B. The fixture 10 can be loaded with four pairs of holders 13, but just one pair is shown here, each holder pair 13 present being carried on a mounting rods 20 of holder base 12A or 12B.

The holder bases 12A, 12B can be designed with more mounting rods 20, so more pairs of holders can be attached and coils 22 can be coated by batch, resulting in a cost-effective and productive process. The coils 22 are attached to the fixture 10 and straightened, by using holders 13 to hold both ends of the coils. However, a portion of coil 22a below spreading member 15 may be bunched up as at 66 into a wad of curved, bunched embolic coil portions (FIG. 8) in its natural manner. The spreading member 15 has a small hole through which a coil goes, member 15 being fixed to the supporting bar 11. The spreading member 15 is used to help spread coils out straight, and to make sure coils are vertical and straight at the moment of coils' emergence from the coating solution in container 17, since it is very important to take coils out of the coating solution of container 17 vertically and straight for achieving uniform coating. Due to usage of the straightening (spreading) member 15 and weight of coils 22, coils can be kept straight and vertical when the coils are taken out from solution, and there is no need to immerge (immerse) spreading coils into solution, (fully spread to their entire, outstretched length) which would need a larger solution container if coils are much longer. The range adjuster 16 (FIG. 1) is used to adjust (and limit) the moving range of the supporting bar based on the length of coated coils.

One advantage of the invention is that the fixture 10 with coils as a whole can be used in coating processes and other added processes, such as: second coating, drying or annealing, and there is no need to de-attach and load coils for each stage. Another advantage of the invention is that the fixture 10 can be used to coat coils with different lengths, due to the movable (slideable) feature of the holder base 12A. The holder base 12B, the supporting bar 11, spreading members 15 and holders 13 may be constructed of stainless steel, Teflon, or coated Teflon, for example.

The invention includes a method to coat coils. The range adjuster 16 is located and fixed based on the length of the coated coils being processed. The holder base 12A is set to a lower, loading position by adjusting the locating pin 14, as in FIG. 2. Up to four coils may be attached to the fixture 10 by using holders 13 carried on mounting rods 20, to secure coils at both ends. Each coil 22 goes through a hole 41 (FIG. 5) of spreading member 15. Due to the weight of coils, the part of coil 22 between the spreading member 15 and the top holders 13 is straight, while the coil portion 22a below spreading member 15 may be naturally folded or bunched up in the normal manner of the particular coil being processed.

One attaches the fixture 10 to a frame (not shown) with the holder base 12A attached to supporting bar 11. The solution container 17, driven by a linear motion (not shown here), is moved up until all coils of embolic coil 22 immerge (immerse) into the solution, and the bottom of supporting bar 11 can sit down on, essentially in contact with, the bottom 24 of the container 17. Remove (loosten) the locating pin 14, and let the solution container 17 move downwardly by a specified speed. As the container 17 moves down, driven by a linear motion, the supporting bar 11 also moves downwardly along with the container 17, but holder base remains at a constant level, held by the frame. The spreading member 15 gradually spreads out the part of coils which is above the spreading member 15 with the help of the weight of coils 22, as coil portions pass through the spreading member aperture 41.

At this moment, partially spread coils vertically emerge out of the solution in container 17. The container 17 and the supporting bar 11 continue to move downwardly until the range adjuster 16 stops the descent of supporting bar 11 by engaging holder base 12a. The container 17 still moves downwardly, until the whole embolic coil or coils 22, and the fixture 10, are out of the solution.

One then takes off the fixture 10 from the frame (not shown) for an optional next process. The coils need to be kept straight in order to prevent from sticking due to the undried coating.

Another method included in the disclosure is to employ the fixture 10 during coating coils by spraying. In the method disclosed here, the holder base 12A is set to a fixed position based on the length of coated coils. Both ends of a coil are secured by holders 13. Instead of using a solution container 17, a spraying nozzle (not shown) is used to apply the coat to coils. The supporting bar 11 is driven to turn around its axis by a motor (not shown) and to move up and down by a linear motion (not shown). The distance between the spraying nozzle and the fixture 10, and the spinning and moving speeds of the supporting bar 11 are varied in order to optimize the spraying process. When coils 22 move up and down, and turn around with the supporting bar 11, polymer solution is sprayed to the coils.

Referring to FIG. 4, the design of coil holders 13 is shown. Each holder 13 is attached to a tubular attachment 40, which can be placed upon a mounting rod 20, which rod enters into lumen 42 to secure holder 13. This supplies support for both the case of the upper holder and the lower holder 13. Each holder 13 comprises a pair of split jaws 44 mounted in lateral port 46. Outer sleeve 48 is mounted on lateral port 46 and held outwardly by the action of spring 50. The respective sloping surfaces 52 on mounting tube 48 and split jaws 44 serves to bias the split jaws 34 in a closed position.

An end of embolic coil 22 may be attached by manually lowering sleeve 48 to permit split jaws 44 to open a slight degree, so that an end of embolic coil 22 can fit therein. Upon release, embolic coil is retained between the split jaws 44, with the retention being biased by spring 50.

Figure 6:
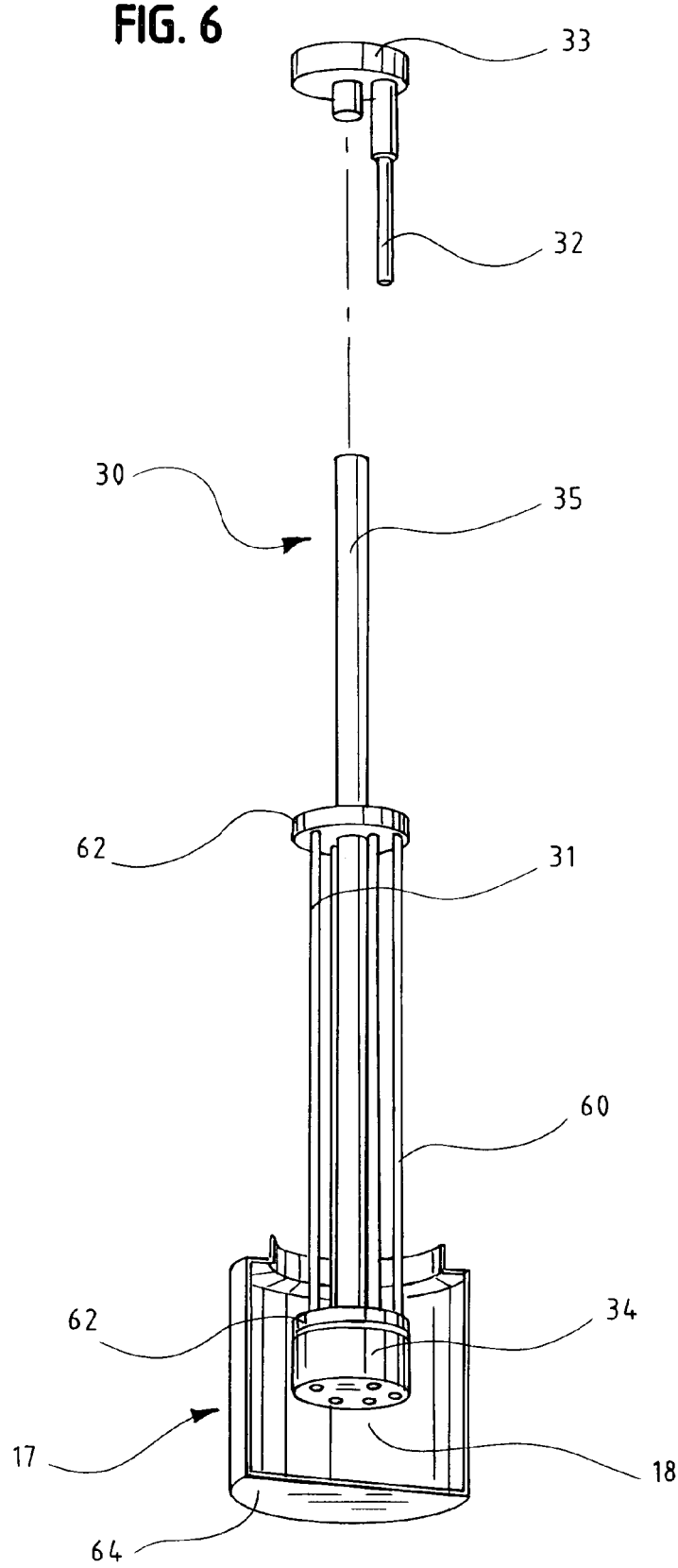
FIG. 6 is a perspective view of another embodiment of the fixture of this invention for supporting and mounting embolic coils, with portions broken away.
Figure 7:
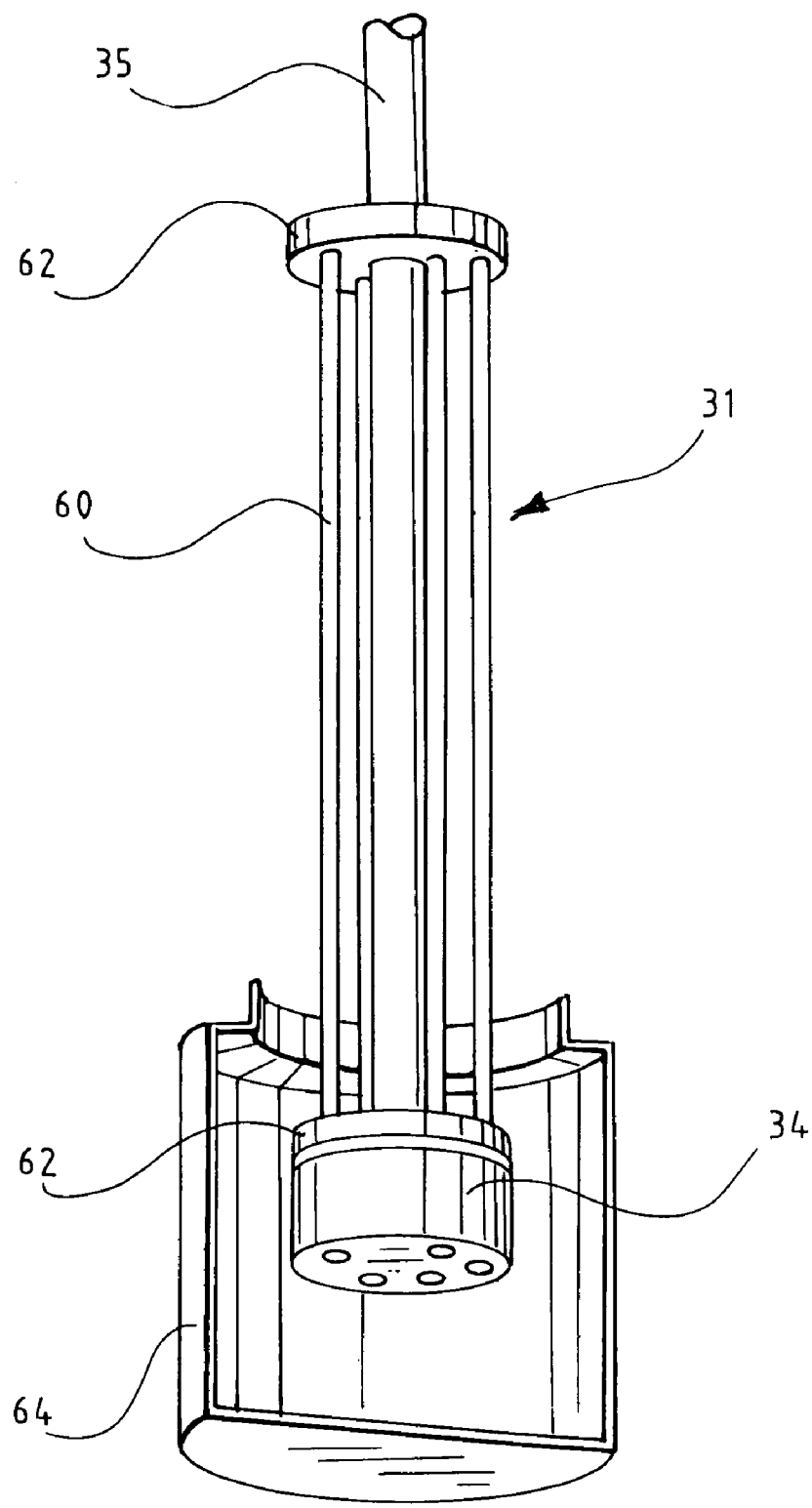
FIG. 7 is an enlarged, fragmentary perspective view of the apparatus of FIG. 6.
Figure 8:
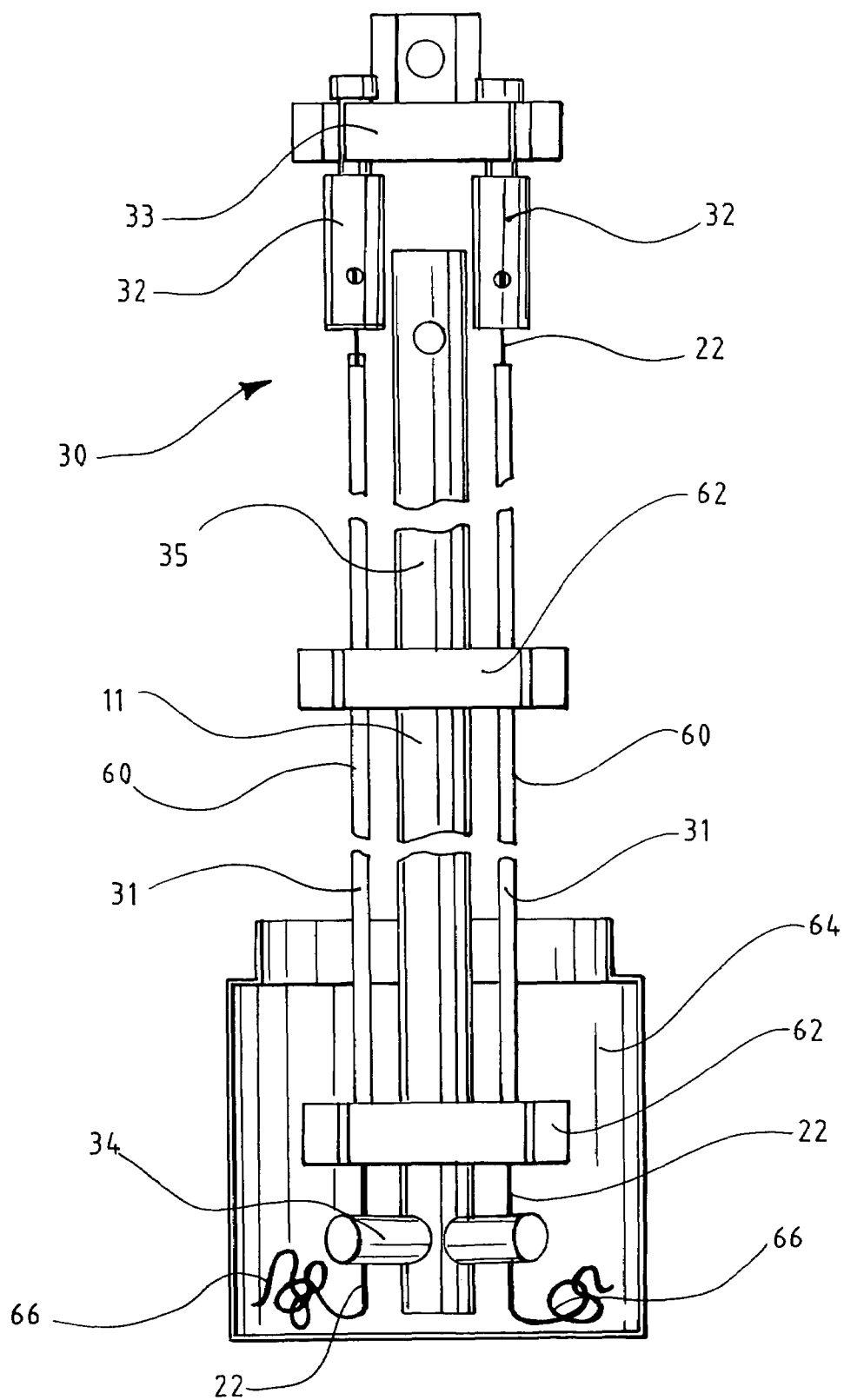
FIG. 8 is a diagrammatic, elevational view of an embodiment of an apparatus similar to that of FIGS. 6 and 7.

In another embodiment of the invention, the fixture can be designed as shown in FIGS. 6-8. Referring to FIGS. 6-8, the fixture 30 for supporting and mounting coils is illustrated to include a tube assembly 31, upper holders 32, holder base 33, and a spreading member 34. The tube assembly 31 is attached to a frame (not shown here) and includes a central supporting bar 35, four tubes 60 for holding coated embolic coils, and two tube discs 62 for mounting the tubes. The lengths of tubes 60 depend on the coated parts' lengths. By designing more mounting holes in the tube discs 62, more tubes can be attached. The holder base 33 is connected to a linear motion device (not shown here) and drives the holders 32 to move up and down. The upper end of each embolic coil 22 is attached to the holders 32 for holding and pulling purposes during coating. The spreading member 34 has small holes through which coils 22 extend, and is fixed to the frame (not shown here). The spreading member 34 is used to spread coils out from bunched coil 66. The fixtures 10, 30 as a whole can be used in coating process and other processes, such as drying, or second coating, or annealing. Fixtures 10, 30 can be also used to coat coils of different lengths. The tube assembly 31, and the holders 32, and the spreading member 34 are constructed of stainless steel, Teflon, or coated Teflon, for example.

In use, the designs of FIGS. 6 through 8 operate in a manner similar to the previous designs of FIGS. 1-5. A container 64 of polymeric coating formulation in a solvent is provided. Fixture 30, with embolic coils 22 attached to upper holders 32, (FIG. 8) rises, drawing lengths of the bunched up portions 66 of embolic coils 22 through an aperture in the spreader or spreaders 34 to provide the portions of embolic coil 22 above spreaders 34 a vertical, straight position. They pass through the respective tubes 31 and the entire frame 30, embolic coils 22 being drawn upwardly, while spreaders 34 stay in the same, desired position. Then, when substantially all portions of the embolic coils 22 have been drawn upwardly out of the solution in container 64, the entire fixture may be removed for drying, holding the coils vertical, or taken to another station for subsequent processing.

One advantage of the invention is that contact between the holders 32, and coated parts are reduced, and then damage to coated parts and coating defects caused by holding are minimized.

The embodiments of the invention include a method to coat coils. The holders 32 are loaded inside the tubes. Coils are attached to the holders 32. Each coil goes through a spreading member 34. Due to the weight of coils, the part of coils between the spreading member 34 and the holders 32 are straight. Mount the tube assembly 31 to a frame and attach the holders 32 to the holder base 33. The solution container 64 is lifted until all of the coil dips into the solution. As the holder base 33 then moves up, the holders 32 pull the coils 22 upwardly, to go through the spreading members 34 and the tubes of assembly 31, until whole coils 22 come out of the solution and are pulled into the tubes 60. One takes off (removes) the tube assembly 31 from the frame for performing other processes. The coils are kept straight in order to prevent individual coils from sticking together due to undried coating.

Dissolving the polymer in a suitable solvent can make polymer solution. Agitation and/or heat may be needed to make a homogenous solution. It is further stated that the modulation of tissue response can be further modified by addition of low molecular weight species or monomers. Such examples could include addition of glycolide monomer or addition of other low molecular weight materials.

The invention is further disclosed by way of these examples:

EXAMPLE 1a

Preparation of 35/65 PCL/PGA Polymer Solution

A 5% wt./wt. Polymer solution is prepared by dissolving 1 part of 35/65 percent PCL/PGA copolymer (poly(epsilon-caprolactone)/poly(glycolic acid)) with 19 parts of the solvent—1,4 dioxane. The solution is prepared in a flask with a magnetic stir bar. For the copolymer to dissolve completely, it is recommended that the mixture be gently heated to $60\pm5°$ C. and continuously stirred for a minimum of 4 hours but not exceeding 8 hours. A clear, homogenous solution is then obtained by filtering the solution through an extra coarse porosity filter (Pyrex brand extraction thimble with fritted disc) using dry nitrogen to help in the filtration of this viscous solution.

EXAMPLE 1b

Preparation of 45/55 PCL/PGA Polymer Solution

A 1% wt./wt. polymer solution is prepared by dissolving 1 part of 45/55 percent PCL/PGA copolymer with 99 parts of the solvent—1,4-dioxane. The solution is prepared in a flask with a magnetic stir bar. For the copolymer to dissolve completely, it is recommended that the mixture be gently heated to $60\pm5°$ C. and continuously stirred for a minimum of 4 hours but not exceeding 8 hours. A clear, homogenous solution is then obtained by filtering the solution through an extra coarse porosity filter (Pyrex brand extraction thimble with fritted disc) using dry nitrogen to help in the filtration of this viscous solution.

EXAMPLE 2

Device Coating Using a "Clamp" Dip Method

A set of clamps was positioned about 1.5 cm apart in height. Each of the two ends of the coil was clamped on to one of the clamps as in FIG. 1. A 20 ml. vial was filled with one of the solutions prepared in Example 1 to the level indicated, and the filled vial was placed on a movable plane. Drove the plane up until the whole coil (except proximal end) immerses into the solution. Freed the lower clamp so that it can move along with the solution vial. Set the coating speed at −3 mm/s. Drove the vial down to a distance according to the coil length. The coil was coated as the coil emerged from the solution gradually at the set speed. The coated coil then has been dried in a vacuum oven for a half hour. The dried coil was stored under vacuum or nitrogen container.

EXAMPLE 3

Device Coating Using a "Tube" Dip Method

A stainless loader and a Teflon tube were used in this experiment. The loader was slid through a tight-fit sleeve. The one end of the coil was politely pushed into the tip of the loader. The coil then was pulled into the sleeve. This assembly was slid through the Teflon tube which was cut in suitable length according to the coil length and positioned on the fixture. The loader was pushed down to deliver the coil out from the sleeve. Fixed the loader onto the driver. Raised the solution container (solution was prepared in Example 1) until the whole coil (except the proximal end) immersed into the solution. Secure the sleeve so that it can move along with the loader. Started to move the drive up at the speed of −3 mm/s. The coil was pulled out from the solution and into the Teflon tube. The driver was stopped until the distal end of the coil pulled into the tube at least 3 cm away from the low end of the tube. Released the coil from the loader and left the coil in the tube. The tube then was put into a vacuum oven for at least a-half hour to dry the coil. The coil was stored in the tube under vacuum or nitrogen container.

EXAMPLE 4

Device Coating Using a Spray Method

A SCS Spray Coating System was used in this experiment. The coil was attached onto fixture with an adjustable length. The rotation speed range of 0.5 to 3.5 rod/s and pass times of 2 to 10 were conducted in the experiment. Other processing parameters were as following:

Line speed: 2.4 mm/s
Coating Feed Rate, ml/hr: 10
Nitrogen Propellant, l/min: 70
Dwell time, min: 1
Coil length, mm: 100
Pass length, mm 112

The 1% solution (prepared in Example 1b) was used in the experiment.

The above had been offered for illustrative purposes only, and is not intended to limit the scope of the invention of this application, which is as defined in the claims below.

That which is claimed is:

1. A method of applying a polymeric coating to at least one embolic coil, which comprises:

passing one end of the embolic coil through an aperture in a spreading member to straighten the coil;

attaching said one end of the embolic coil to an upper holder positioned above said spreading member, the embolic coil portion that extends from the upper holder to said aperture being generally vertical and straight;

applying to said embolic coil a dispersion of a polymeric coating formulation in a solvent; and passing portions of said embolic coil which are below said spreading member through said spreading member, to cause substantially the entire embolic coil, with said polymeric coating formulation applied, to be vertical and straight;

removing the spreading member and the upper holder while in fixed position relative to each other and removing the embolic coil from further contact with said coating formulation; and drying said embolic coil.

2. The method of claim 1 in which the portion of said embolic coil positioned below said spreading member is generally bunched into a wad of curved, bunched embolic coil portions.

3. The method of claim 1 in which a lower end of said embolic coil is attached to a lower holder, which lower holder is held in fixed position relative to the spreading member.

4. The method of claim 1 in which the dispersion of polymeric coating is applied to the embolic coil by immersion into a container holding said dispersion.

5. The method of claim 4 in which the upper holder rises and the spreading member is stationary and immersed in the dispersion, to pass portions of the embolic coil upwardly through said spreading member, to straighten and hold vertical substantially the entire embolic coil.

6. The method of claim 5 in which the embolic coil is removed from said further contact with the coating formulation by lowering the container of said dispersion.

7. The method of claim 6 in which the lower end of said embolic coil is attached to a lower holder, which lower holder is held in fixed position relative to the spreading member.

8. The method of claim 7 in which the portion of said embolic coil positioned below said spreading member is generally bunched into a wad of curved, bunched embolic coil portions.

9. The method of claim 1 in which a plurality of said upper holders and spreading members are present, holding a plurality of said embolic coils.

10. The method of claim 1 in which said embolic coil is further processed, prior to removal of the coil from the upper holder and spreading member.

11. The method of claim 1 in which said dispersion of a polymeric coating is applied to the embolic coil by a spray.

12. The method of claim 1 in which said embolic coil is held between the spreading member and the upper holder in a manner whereby individual coils of the embolic coil are spaced from each other, to facilitate access of the polymeric coating between the coils.

13. The method of claim 12 in which said coils are spaced by essentially 0.001-0.1 inch.

14. The method of applying a polymeric coating to at least one embolic coil, which comprises:
   attaching one end of the embolic coil to an upper holder positioned above a spreading member;
   passing one end of the embolic coil through an aperture in said spreading member whereby the embolic coil portion that extends from the upper holder to said aperture is generally vertical and straight;
   applying to said embolic coil a dispersion of a polymeric coating formulation in a solvent;
   passing portions of said embolic coil which are below said spreading member through said spreading member, to cause substantially the entire embolic coil, with said polymeric coating formulation applied, to be vertical and straight, said embolic coil positioned below said spreading member being generally bunched into a wad of curved, bunched embolic coil portions;
   removing from said container the embolic coil, held with the spreading member and upper holder, while in fixed position relative to each other, from further contact with said coating formulation; and drying the embolic coil.

15. The method of claim 14 in which said step of applying said dispersion comprises immersing said embolic coil into a container holding said dispersion in said solvent.

16. The method of claim 15 in which said portions of said embolic coil below said spreading member are passed through said spreading member by raising said upper holder relative to the spreading member.

17. The method of claim 16 in which the lower end of said embolic coil is attached to a lower holder, which lower holder is held in a fixed position relative to the spreading member.

18. The method of claim 16 in which a plurality of said upper holders and spreading members are present, holding a plurality of said embolic coils together in a single fixture.

\* \* \* \* \*